(12) United States Patent
De Prisco et al.

(10) Patent No.: US 9,080,946 B2
(45) Date of Patent: Jul. 14, 2015

(54) DIGITAL ROCK ANALYSIS SYSTEMS AND METHODS WITH MULTIPHASE FLOW REV DETERMINATION

(75) Inventors: Giuseppe De Prisco, Houston, TX (US); Jonas Toelke, Houston, TX (US)

(73) Assignee: Ingrain, Inc., Houston, TX (US)

( * ) Notice: Subject to any disclaimer, the term of this patent is extended or adjusted under 35 U.S.C. 154(b) by 441 days.

(21) Appl. No.: 13/524,758

(22) Filed: Jun. 15, 2012

(65) Prior Publication Data

US 2013/0338976 A1    Dec. 19, 2013

(51) Int. Cl.
*G01V 1/40*      (2006.01)
*G01N 23/225*    (2006.01)
*G06T 7/00*      (2006.01)
*G01N 33/24*     (2006.01)
*G06T 7/40*      (2006.01)

(52) U.S. Cl.
CPC ........ *G01N 23/2251* (2013.01); *G01N 23/2255* (2013.01); *G01N 33/24* (2013.01); *G06T 7/0004* (2013.01); *G06T 7/401* (2013.01); *G01N 2223/649* (2013.01); *G06T 2207/30132* (2013.01)

(58) Field of Classification Search
None
See application file for complete search history.

(56) References Cited

U.S. PATENT DOCUMENTS

| | | | |
|---|---|---|---|
| 2010/0135536 A1* | 6/2010 | Dvorkin et al. | 382/109 |
| 2010/0198638 A1* | 8/2010 | Deffenbaugh et al. | 705/7 |
| 2011/0004447 A1* | 1/2011 | Hurley et al. | 703/1 |
| 2012/0239361 A1* | 9/2012 | Vargas-Guzman | 703/6 |
| 2014/0058676 A1 | 2/2014 | De Prisco et al. | |

FOREIGN PATENT DOCUMENTS

WO    2013/188239    12/2013

OTHER PUBLICATIONS

Hilpert, Markus, et al.,"Pore-Morphology-Based Simulation of Drainage in Totally Wetting Porous Media", *Advances in Water Resources* 24, (2001), p. 243-255, Elsevier Science Ltd.
PCT International Preliminary Report on Patentability, dated Sep. 24, 2014, Appl No. PCT/2013/044773, "Digital Rock Analysis Systems and Methods with Multiphase Flow REV Determination," Filed Jun. 7, 2013, 17 pgs.
PCT International Search Report and Written Opinion, dated Nov. 26, 2013, Appl No. PCT/US13/44773, "Digital Rock Analysis Systems and Methods with Multiphase Flow REV Determination," filed Jun. 7, 2013, 27 pgs.

(Continued)

*Primary Examiner* — Aditya Bhat
(74) *Attorney, Agent, or Firm* — Krueger Iselin LLP

(57) ABSTRACT

The pore structure of rocks and other materials can be determined through microscopy and subject to digital simulation to determine the properties of multiphase fluid flows through the material. To conserve computational resources, the simulations are preferably performed on a representative elementary volume (REV). The determination of a multiphase REV can be determined, in some method embodiments, by deriving a porosity-related parameter from a pore-matrix model of the material; determining a multiphase distribution within the material's pores; partitioning the pore-matrix model into multiple phase-matrix models; and deriving the porosity-related parameter from each phase-matrix model. The parameter's dependence on phase and saturation can then be determined and analyzed to select an appropriate REV size.

20 Claims, 7 Drawing Sheets

(56) References Cited

OTHER PUBLICATIONS

Adalsteinsson, David et al., "Accurate and Efficient Implementation of Pore-Morphology-based Drainage Modeling in Two-dimensional Porous Media", Transport in Porous Media (2006) 65: 337-358, © Springer 2006, DOI 10.1007/s11242-005-6091-6.

Hazlett, R. D., "Simulation of Capillary-Dominated Displacements in Microtomographic Images of Reservoir Rocks", Transport in Porous Media 20:21-35, 1995, 15 pgs., KluwerAcademic Publishers. Printed in the Netherlands.

Liu, Jie et al., "Application of Percolation Theory to Microtomography of Structured Media: Percolation Threshold, Critical Exponents, and Upscaling", Physical Review E 83, 016106 (2011), 13 pgs., American Physical Society, 1539-3755/2011/83(1)/016106(13).

Liu, Jie et al., "Improved Estimates of Percolation and Anisotropic Permeability From 3-D X-ray Microtomography Using Stochastic Analyses and Visualization", Geochemistry Geophysics Geosystems (G3), May 29, 2009, 13 pgs., vol. 10, No. 5, American Geophysical Union (AGU) and the Geochemical Society, An Electronic Journal of the Earth Sciences.

Papatzacos, Paul, "Cellular Automaton Model for Fluid Flow in Porous Media", Complex Systems 3 (1989), pp. 383-405, Complex Systems Publication, Inc.

* cited by examiner

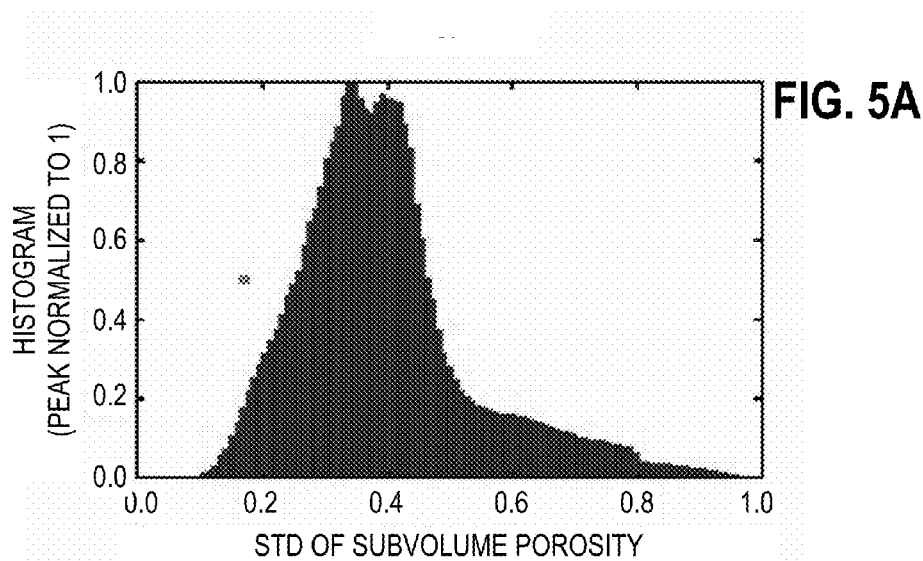
FIG. 5A
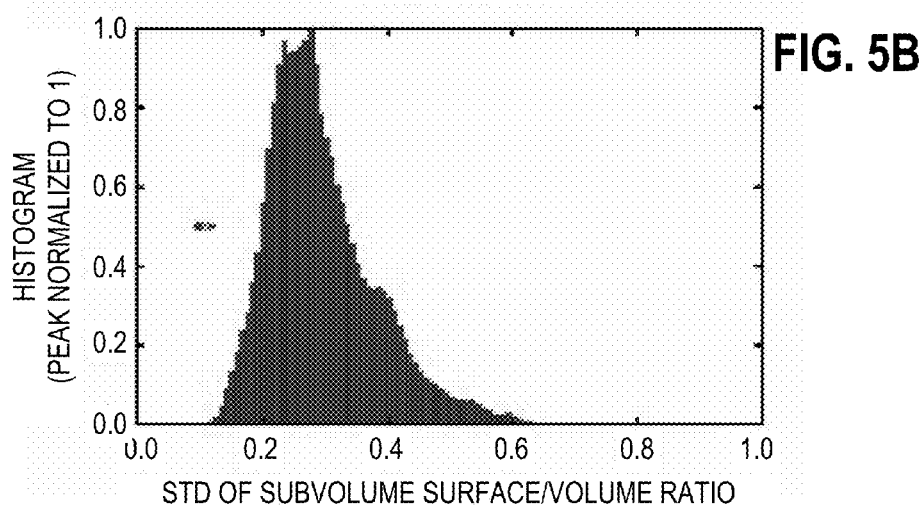
FIG. 5B
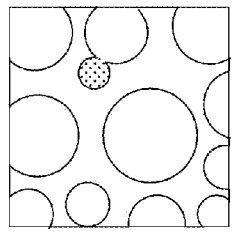 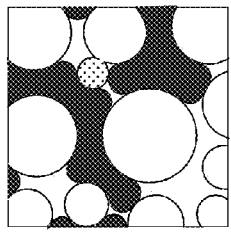 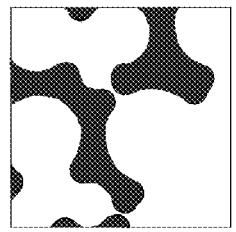 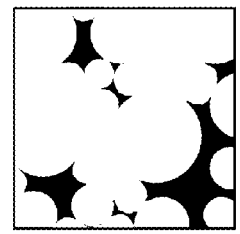
FIG. 6A  FIG. 6B  FIG. 6C  FIG. 6D

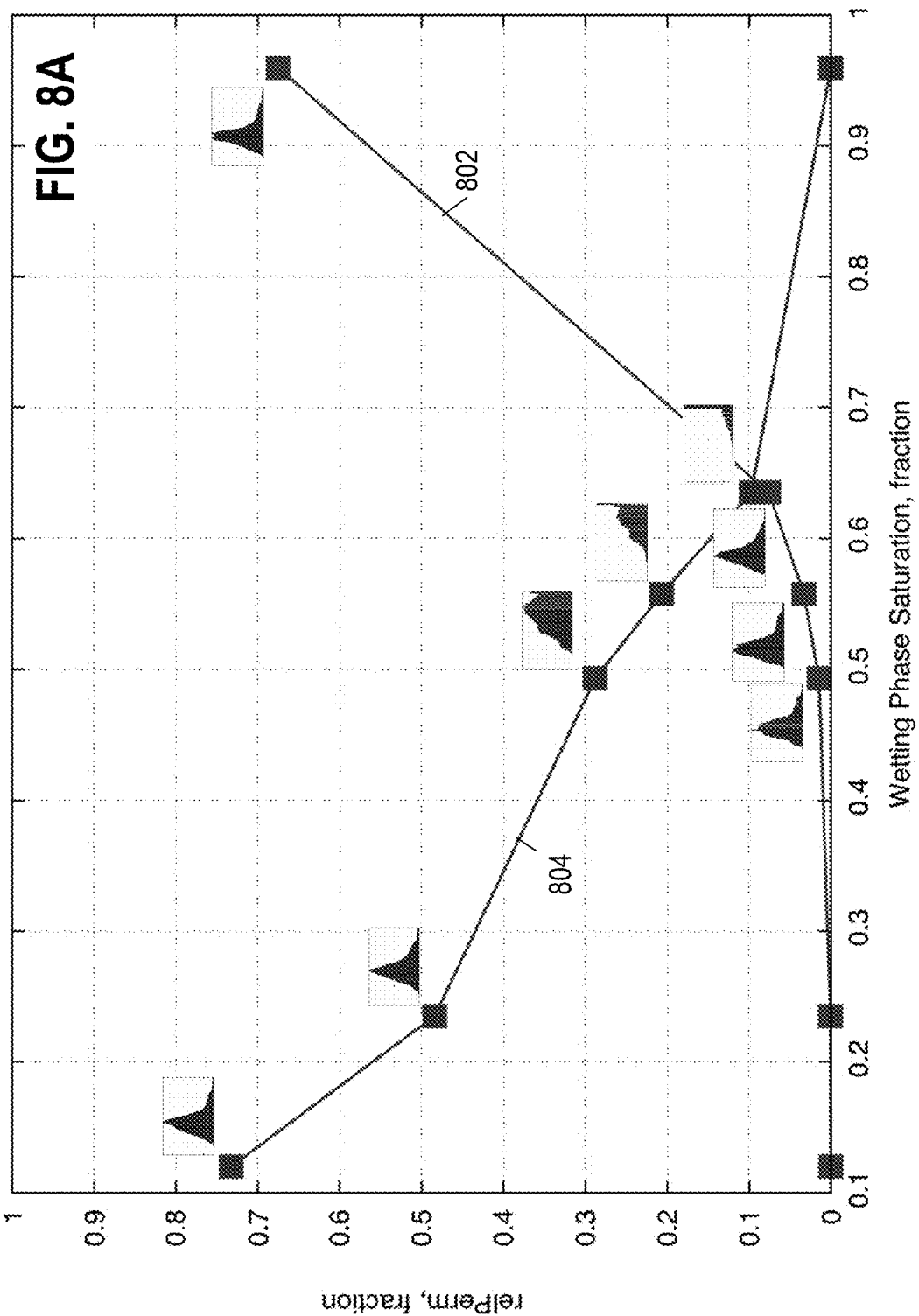

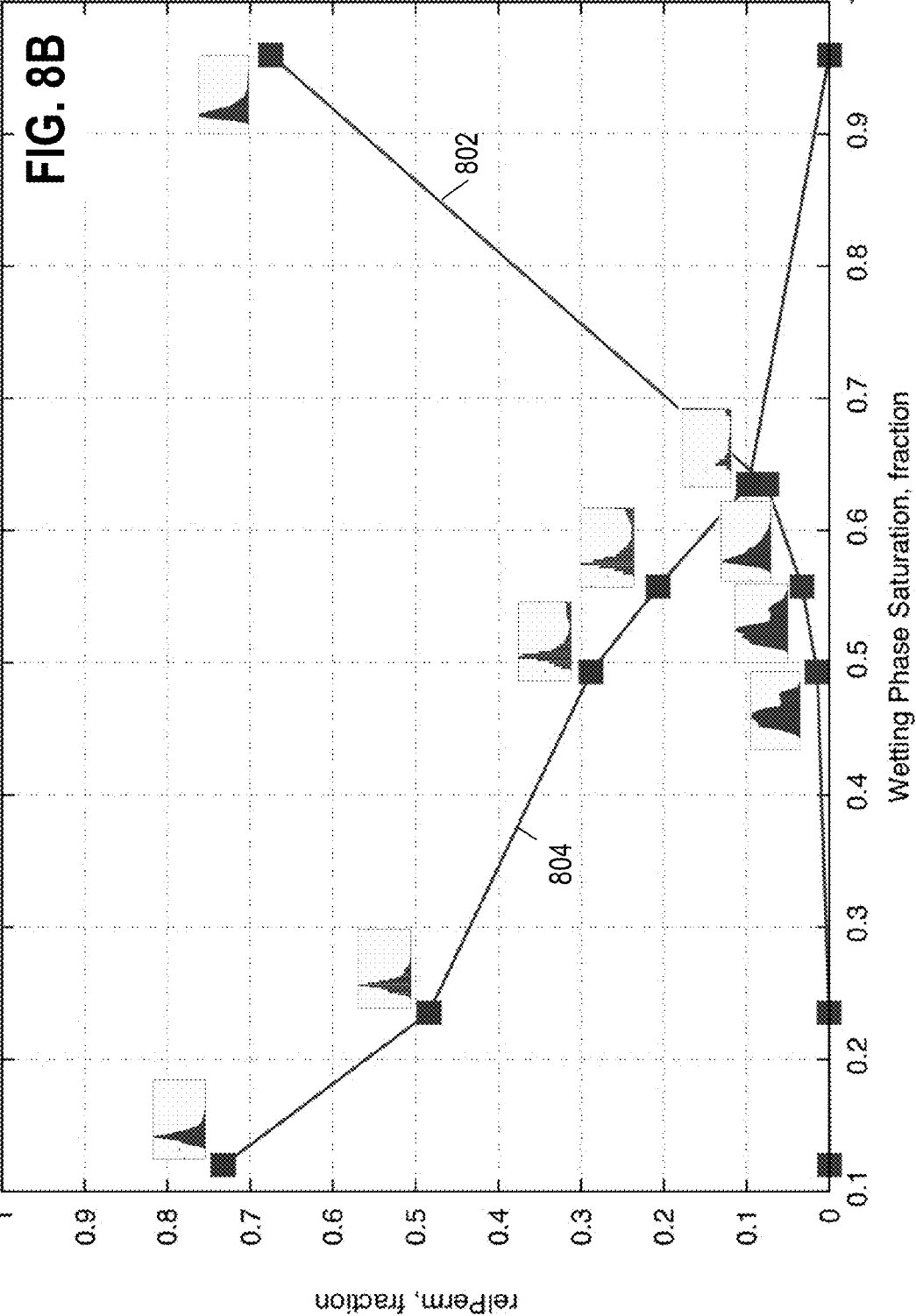

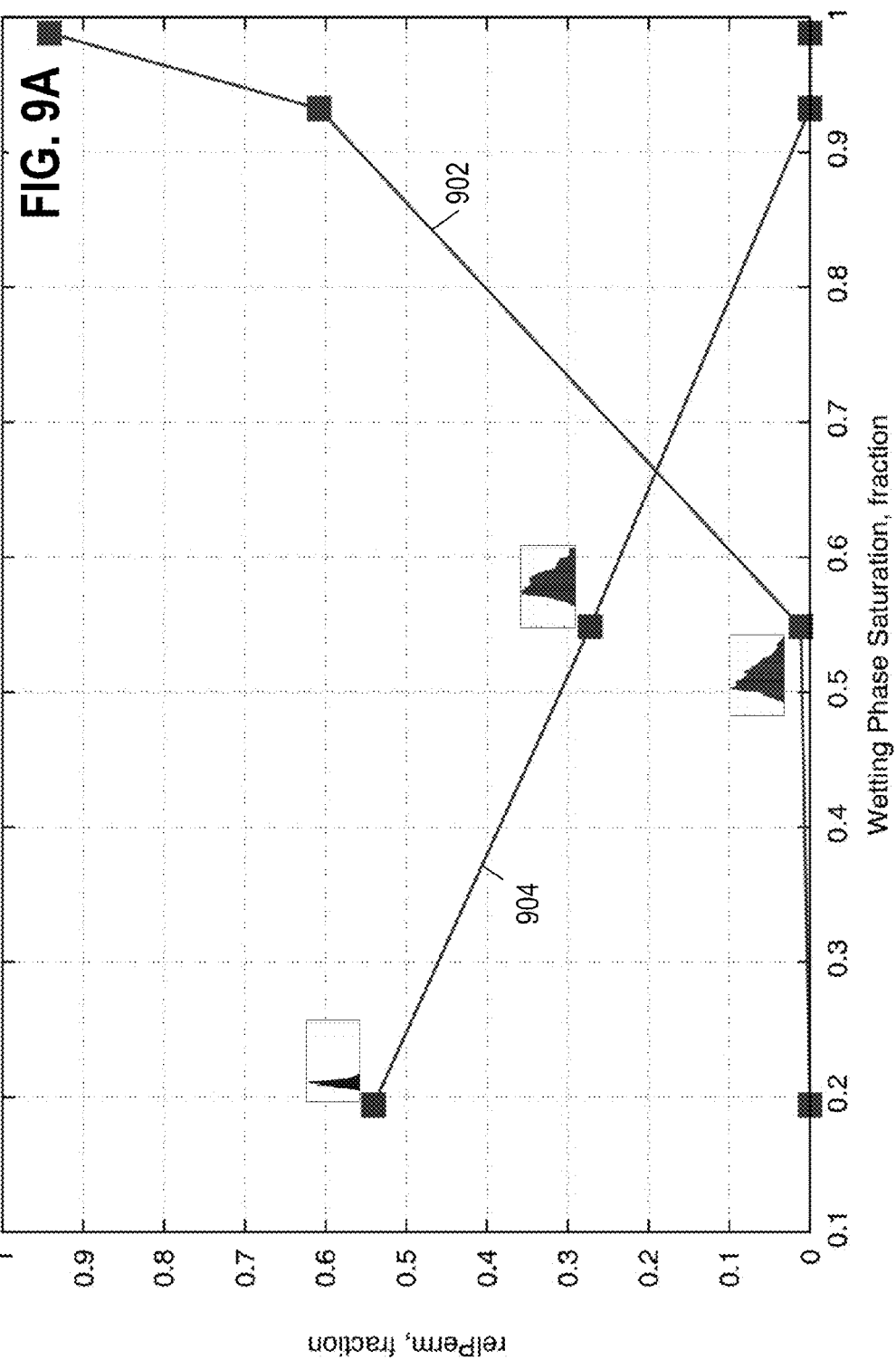

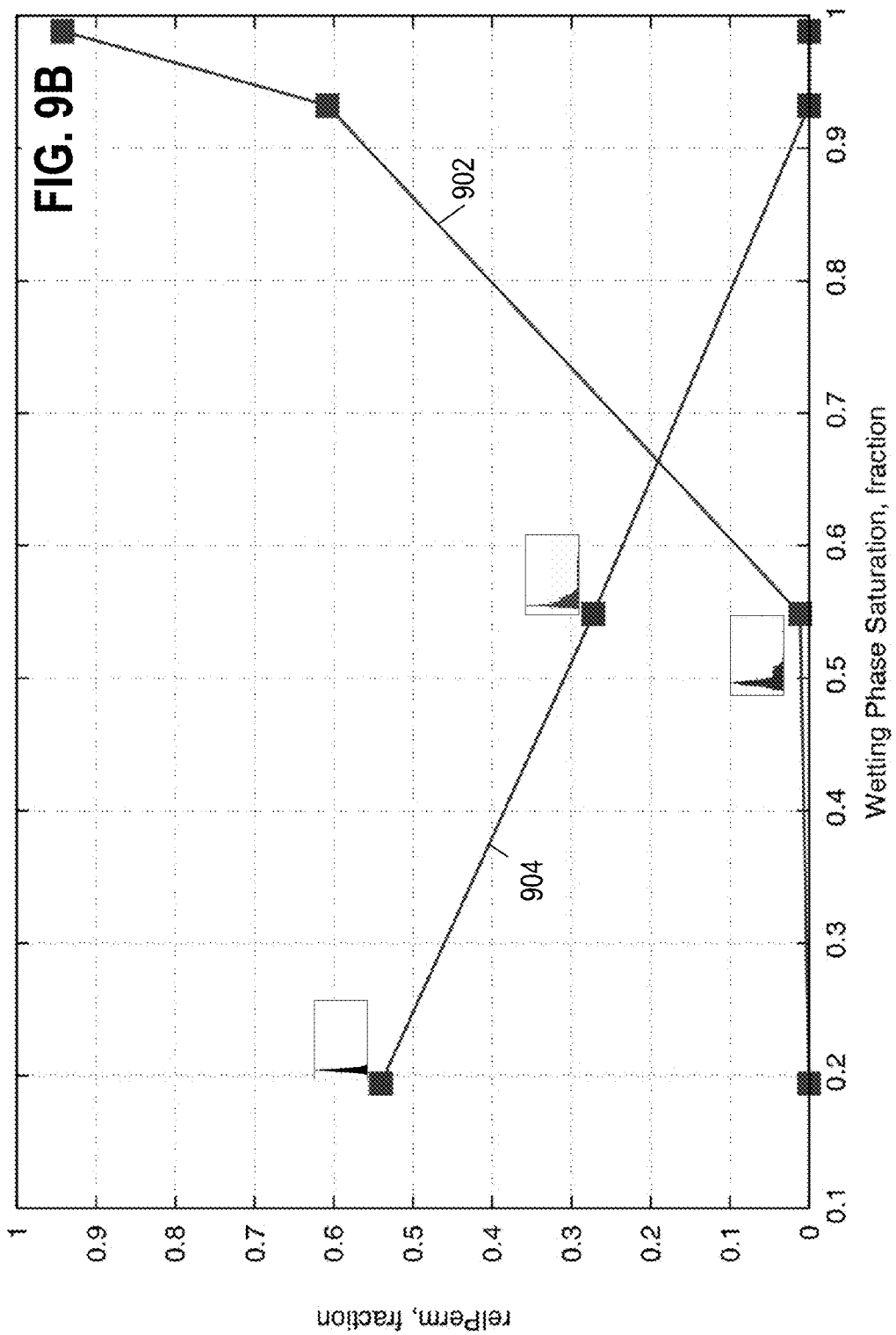

DIGITAL ROCK ANALYSIS SYSTEMS AND METHODS WITH MULTIPHASE FLOW REV DETERMINATION

BACKGROUND

Microscopy offers scientists and engineers a way to gain a better understanding of the materials with which they work. Under high magnification, it becomes evident that many materials (including rock and bone) have a porous microstructure that permits fluid flows. Such fluid flows are often of great interest, e.g., in subterranean hydrocarbon reservoirs. The possibility of characterizing materials in terms of porosity, permeability, and saturation is well known, but such characterizations inevitably fail at a scale where the material is too anisotropic and/or heterogeneous to be characterized as a homogeneous medium.

Naturally, it is of interest to know the size at which a sample of the material becomes representative of the whole. The smallest volume over which a given measurement can be made that yields a value representative of larger volumes is termed a representative elementary volume ("REV"). Note that the REV depends on the selected measurement.

A number of references purport to determine the REV, but suffer from one or more shortcomings including subjectivity, error, over-estimation, overly-generous search regions, overly-restrictive subvolume positioning, inability to cope with sample heterogeneity, and inapplicability of the selected measurement to the intended use of the REV (e.g., multiphase fluid flow simulation).

BRIEF DESCRIPTION OF THE DRAWINGS

Accordingly, there are disclosed herein digital rock analysis systems and methods with multiphase flow representative elementary volume ("REV") determination. In the drawings:

FIGS. 5A-5B show illustrative sample parameter distributions.

FIGS. 6A-6D illustrate a phase-based partitioning of porosity.

FIGS. 8A-8B show the parameter distribution changes as a function of saturation for phase-partitioned porosities for a first illustrative sample.

FIGS. 9A-9B show the parameter distribution changes as a function of saturation for phase-partitioned porosities for a second illustrative sample.

Figure 1:
FIG. 1 shows an illustrative high resolution focused ion beam and scanning electron microscope.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

For context, FIG. 1 provides an illustration of a high-resolution focused ion beam and scanning electron microscope 100 having an observation chamber 102 in which a sample of material is placed. A computer 104 is coupled to the observation chamber instrumentation to control the measurement process. Software on the computer 104 interacts with a user via a user interface having one or more input devices 106 (such as a keyboard, mouse, joystick, light pen, touchpad, or touchscreen) and one or more output devices 108 (such as a display or printer).

For high resolution imaging, the observation chamber 102 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

The system described above is only one example of the technologies available for imaging a sample. Regardless of how the images are acquired, the following disclosure applies so long as the resolution is sufficient to reveal the porosity structure of the sample.

Figure 2:
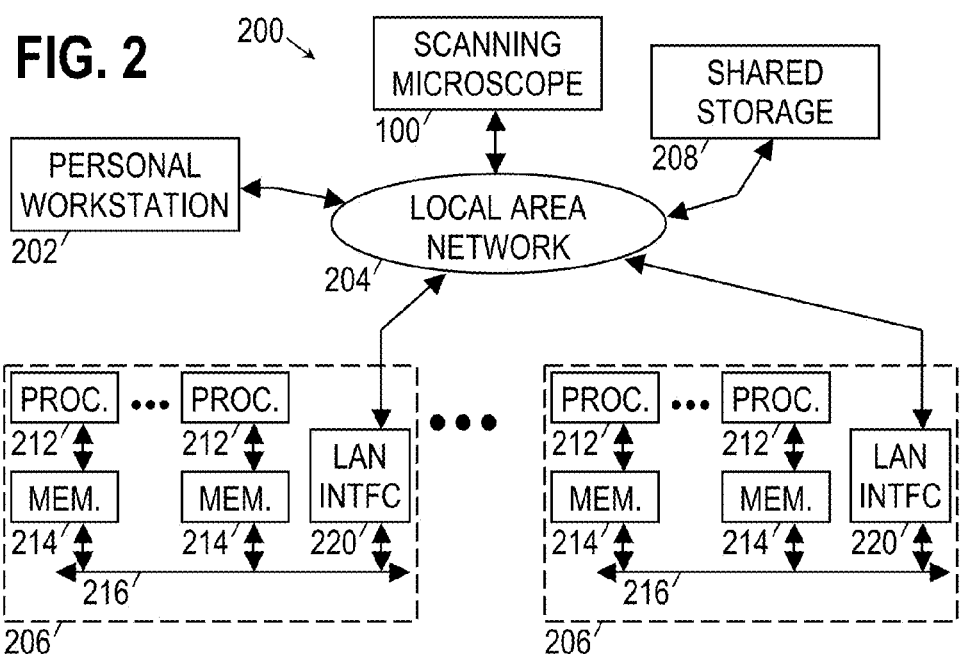
FIG. 2 shows an illustrative high performance computing network.

FIG. 2 is an example of a larger system 200 within which the scanning microscope 100 can be employed. In the larger system 200, a personal workstation 202 is coupled to the scanning microscope 100 by a local area network (LAN) 204. The LAN 204 further enables intercommunication between the scanning microscope 100, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the scanning microscope. For tasks having small computational demands, the software may be executed on the personal workstation 202, whereas computationally demanding tasks may be preferentially run on the high performance computing platform 206.

Figure 3:
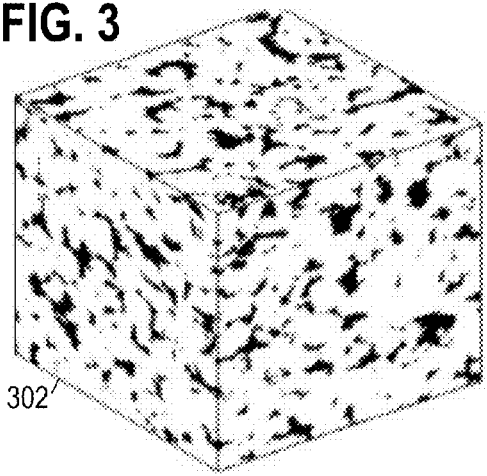
FIG. 3 shows an illustrative volumetric representation of a sample.

FIG. 3 is an illustrative image 302 that might be acquired by the scanning microscope 100. This three-dimensional image is made up of three-dimensional volume elements ("voxels") each having a value indicative of the composition of the sample at that point.

Figure 4:
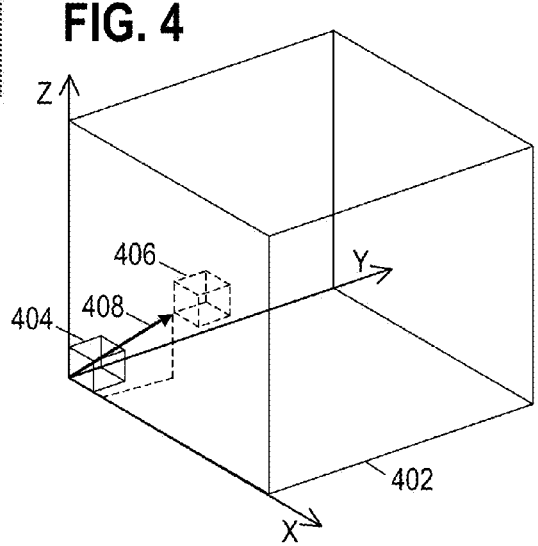
FIG. 4 shows an illustrative coordinate system for performing sample analysis.

FIG. 4 provides a coordinate system for a data volume 402, with the x-, y-, and z-axes intersecting at one corner of the volume. Within the data volume, a subvolume 404 is defined. The illustrated subvolume 404 is a cube having sides of length a, but other subvolume shapes may alternatively be used, e.g., a parallelogram having the same shape as the overall data volume, a sphere, or a tetrahedron. It is desirable, though not necessary, for the chosen subvolume shape to be scalable via a characteristic dimension such as diameter or length of a side. The subvolume 404 can be defined at any position 406 within the data volume 402 using a displacement vector 408 from the origin to a fixed point on the subvolume. Similarly, sub-subvolumes can be defined and positioned within each subvolume.

One way to characterize the porosity structure of a sample is to determine an overall parameter value, e.g., porosity. The image is processed to categorize each voxel as representing a pore or a portion of the matrix, thereby obtaining a pore-matrix model in which each voxel is represented by a single bit. The total porosity of the sample can then be determined with a straightforward counting procedure. However, the resulting number reveals little about the structure, heterogeneity and isotropy of the sample. Accordingly, a more sophisticated measure may be preferred.

FIG. 5A shows a histogram of the standard deviation of subvolume porosity (or surface/volume or any other quantity that can be computed in a slice of the subvolume) in an illustrative carbonate rock sample, as calculated along a specific direction (the flow direction). The standard deviation is evaluated with respect to the average porosity (or surface/volume or other global quantity) of the whole data volume. Note that the distribution is a function of the length scale l used to define the subvolume. For each possible position of a subvolume of length scale l within the data volume, a standard deviation of a quantity that can be computed in a transverse slice is evaluated along the specific direction. In other words, one standard deviation calculation indicates the variation of a specific subvolume's porosity (or other quantity that can be computed in a slice) with respect to the averaged porosity of the whole volume in the given flow direction, normalized by the average porosity for the whole volume. The calculation of standard deviation is repeated for each possible position of the subvolume within the whole volume, yielding a set of standard deviations that are going to build the distribution of the standard deviations of the specific quantity that can be computed in a slice for the specific length scale of the subvolume and fixed direction. The set of standard deviations for subvolume porosity is plotted in a histogram in FIG. 5A, indicating a fairly consistent degree of heterogeneity with a gradual tail on the high side.

If this operation is repeated for different subvolume length scales, different histograms will be obtained, so that a statistical function of the length scale can be obtained. The moments of the distribution (mean, variance, kurtosis and skewness) can be evaluated to check at which length scale the distribution stabilizes (i.e., the statistic converges). The REV can be defined in terms of the length scale value where convergence is reached. Often when convergence is reached, the distribution moments approach those of a Gaussian distribution (and the histogram looks Gaussian).

FIG. 5B shows a similar histogram for the standard deviation of the subvolume surface/volume ratio. This ratio provides an indication regarding the size of the pores, and the standard deviation histogram indicates a dominant, consistent mode of heterogeneity with a suggestion of a second, smaller heterogeneity mode on the higher end.

As explained in U.S. Provisional Application 61/618,265 titled "An efficient method for selecting representative elementary volume in digital representations of porous media" and filed Mar. 30, 2012 by inventors Giuseppe De Prisco and Jonas Toelke (and continuing applications thereof), either or both of these measures can be employed to determine whether reduced-size portions of the original data volume adequately represent the whole for porosity- and permeability-related analyses.

A potential difficulty arises, however, in analyses concerning multiple fluid phases effectively occupying different parts of the pore space. To understand why this is so, please consider FIGS. 6A-6D. FIG. 6A shows an illustrative sample image having pore space between circularly shaped grains of matrix material. Taking the white pore space as being filled with a wetting fluid phase (e.g., water), consider invasion by a second, non-wetting phase (e.g., oil). In accordance with Laplace's equation, a positive capillary pressure produces a spherical interface having a curvature radius that shrinks with increased pressure, yielding a pressure-related degree of invasion into the pores.

FIG. 6B shows the sample of FIG. 6A with the addition of an invading (non-wetting) fluid phase shown as black. It can be seen that the pore space has been partitioned. FIG. 6C shows the pore space filled by the non-wetting phase (in black) while FIG. 6D shows the pore space filled by the wetting phase (in black). The pore-matrix model is thus partitioned into two phase-based pore-matrix models, hereafter termed phase-matrix models. This process can be readily extended, with an additional pore-matrix model obtained for each additional (non-mixing) phase. More information on an illustrative partitioning process can be found in Hilpert and Miller, "Pore-morphology-based simulation of drainage in totally wetting porous media", Advances in Water Resources 24 (2001) 243-255.

The partitioning is a function of the manner (injection, drainage, invasion), history, and degree of simulated fluid movement. In one illustrative implementation, spheres of gradually decreasing diameter, that here represent a perfect non-wetting fluid having negligible viscous coupling with other phases, are used to invade the pore space from one or more edges of the data model. The gradually decreasing diameter enables the invading fluid to reach more of the pore space, depending on the size and connectivity. In other implementations, connectivity may not be required, and fluid invasion permitted anywhere the requisite spheres will fit, the sphere diameters gradually increasing to yield less and less of the pore space to be occupied by the non-wetting fluid.

At each step (i.e., each sphere diameter), the corresponding phase-matrix models are determined and subject to separate analyses. For example, each pore-matrix model may be subject to a separate determination of porosity, permeability, surface-to-volume ratio, histogram of standard deviation of porosity, histogram of standard deviation of surface-to-volume ratio, and/or characteristic dimension of an REV. For example, an absolute permeability $k_{p,s}^{abs}$ can be computed from each phase-matrix model, where p is the phase (e.g., wetting or non-wetting) and s is the saturation of that phase as measured at the current invasion step in the original pore-matrix model. See, e.g., Papatzacos "Cellular Automation Model for Fluid Flow in Porous Media", Complex Systems 3 (1989) 383-405. From the computed absolute permeability values, we can obtain a (quasi static) relative permeability $k_{p,s}^{rel} = k_{p,s}^{abs}/k^{abs}$, where the denominator is the absolute permeability $k^{abs}$ of the original pore-matrix model. This calculation assumes a strong uniform wettability and negligible viscous coupling between the two phases, i.e., it represents the quasi-static relative permeability.

The carbonate rock sample that was used to determine the histograms in FIGS. 5A-5B was subjected to this analysis, yielding the static relative permeability vs. saturation curves shown in FIGS. 8A-8B. In both figures, curve 802 shows the quasi static relative permeability vs saturation for the wetting phase, while curve 804 shows the quasi static relative permeability vs saturation for the non-wetting phase. Insets in FIG. 8A show histograms of the standard deviation for subvolume porosity, while insets in FIG. 8B show histograms of the standard deviation for subvolume surface/volume ratio. The insets at high relative permeability values can be compared with FIGS. 5A-5B to confirm that the distributions match when the pores are largely occupied by either single phase.

As the nonwetting phase saturation falls from near 1 to about 0.5 (shown in the figure as wetting saturation near 0 and 0.5, respectively), the histogram of standard deviation of porosity broadens and moves upward, indicating greatly increased heterogeneity. In other words, the network of porosity that the non-wetting fluid is forming for lower non-wetting saturation invades only parts of the pore space, and that leads to the heterogeneous distribution. The histogram of standard deviation of surface to volume ratio and porosity shows a growing peak at the right side of the graph for the non-wetting phase curve, probably indicating the presence of large heterogeneities.

As the wetting phase saturation falls from near 1 to about 0.5, the histogram of standard deviation of porosity for the wetting phase remain a consistent match to the original distribution. This observation suggests that as soon as the wetting phase is flowing, it can access almost any part of the pore space. The histogram of standard deviation for surface-to-volume ratio acquires additional peaks, revealing the increased heterogeneity from the reduced amount of wetting phase.

To perform a multiphase REV analysis, the histograms at multiple saturations and different length scales should be compared to the corresponding histograms of the original data volume to determine at which length scale there is the same rate of convergence of the moments of the distributions. The smallest data volume for which the histograms show an adequate match may be considered a representative elementary volume for multi-phase analyses. In other words, the length scale at which moments of the distribution for different saturations converge at the same rate corresponds to the multiphase REV.

Where the histograms are consistent across a wide saturation range (e.g., the wetting phase in this carbonate rock example), one can be reasonably confident that at the specific length scale the spreading of wetting and non-wetting phase is not dependent on the saturation level. Starting at that length scale, the convergence of the moments of the distribution can be compared for each saturation level at larger length scales to identify the multiphase REV size FIGS. 9A-9B show the quasi-static relative permeability vs. saturation curves for a second carbonate rock example. In both figures, curve 902 represents the wetting phase and curve 904 represents the non-wetting phase. The insets in FIG. 9A show the histograms for the standard deviation of subvolume porosity, whereas the insets in FIG. 9B show the histograms for the standard deviation of subvolume surface-to-volume ratio. The available results suggest that the standard deviation distributions (of both porosity and Surface/Volume) have the same spreading and same mode for wetting and non-wetting phase, indicating basically that the two phases are going to distribute in a similar way throughout the porosity of the sample for each saturation level. A length scale dependence analysis can be started in order to define, as explained in U.S. Provisional Application 61/618,265 titled "An efficient method for selecting representative elementary volume in digital representations of porous media" a good REV.

In general, different fractional flows may require different simulation volumes: for small fractional flow of the non-wetting phase the REV dimension may increase. This is not expected for the wetting phase that, instead, invades the pore space in a more homogeneous way as soon as it starts to flow.

Figure 7:
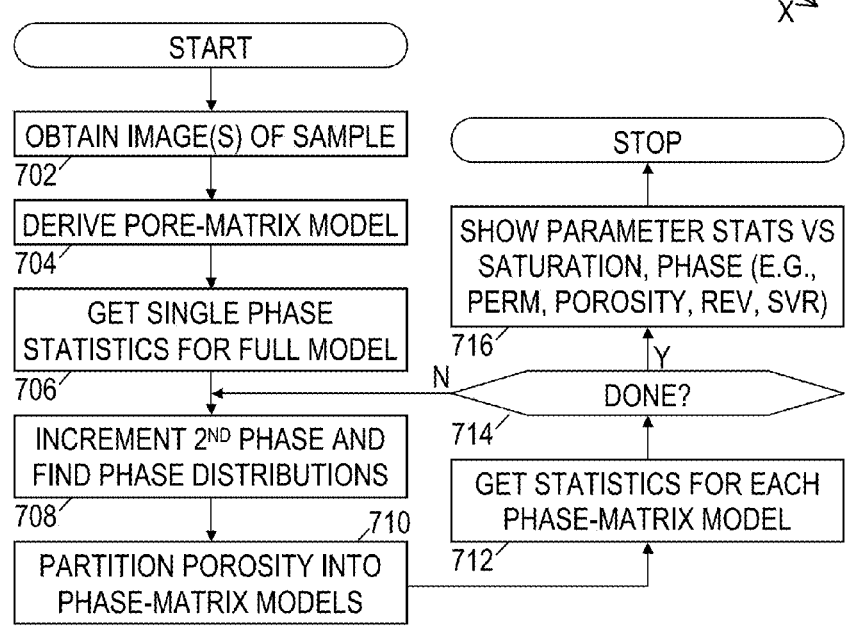
FIG. 7 is a flowchart of an illustrative analysis method.

FIG. 7 is a flowchart that summarizes at least some of the method embodiments disclosed herein. Beginning in block 702, the system obtains one or more images of the sample, e.g., with focused ion beam microscopy. Of course the images can be alternatively supplied as data files on an information storage medium. In block 704, the system processes the images to derive a pore-matrix model. Such processing can involve sophisticated filtering as set forth in existing literature to classify each image voxel as representing a pore or a portion of the matrix. In block 706, the system analyzes the full pore-matrix model to obtain single phase statistics such as, e.g., porosity, surface-to-volume ratio, permeability, histograms of standard deviation of subvolume porosity and surface-to-volume ratio, and REV dimension.

In block 708, the system adds a second phase or increases the saturation of the second phase. As previously discussed, this can be done via a simulated injection, simulated drainage, or other simulated invasion process. In block 710, the system partitions the full pore-matrix model into phase-matrix models to segregate the pore space occupied by the different phases. In block 712, the phase-matrix models are subject to the same analyses as the full pore-matrix model, e.g., porosity, surface-to-volume ratio, permeability, histograms of standard deviation of subvolume porosity and surface-to-volume ratio as a function of subvolume length scale, and REV size.

In block 714, the system determines whether additional saturations need to be evaluated, and if so, blocks 708-714 are repeated. Once each desired saturation point has been evaluated, the system shows the statistics as a function of phase and saturation in block 716 to enable the user to determine an appropriate REV for multiphase calculations.

Numerous variations and modifications will become apparent to those skilled in the art once the above disclosure is fully appreciated. For example, the foregoing disclosure describes illustrative statistics for determining an REV size, but other suitable statistics exist and can be employed. It is intended that the following claims be interpreted to embrace all such variations and modifications.

What is claimed is:

1. A digital rock analysis method that comprises:
deriving from a pore-matrix model at least one pore structure parameter;
determining a distribution of multiple phases within pores of the pore-matrix model;
based on said distribution, partitioning the pore-matrix model into multiple phase-matrix models;
deriving said at least one pore structure parameter from each of the phase-matrix models; and
producing a representation of the at least one pore structure parameter's dependence on said distribution.

2. The method of claim 1, wherein the at least one pore structure parameter comprises:
a distribution of standard deviation of subvolume porosity and a distribution of standard deviation of subvolume pore surface-to-volume ratio.

3. The method of claim 2, further comprising adjusting a subvolume length scale until moments of said distributions of standard deviation converge to indicate a representative elementary volume (REV) size.

4. The method of claim 1, further comprising converting one or more images of a sample into said pore-matrix model.

5. The method of claim 4, further comprising acquiring said one or more images with a scanning microscope.

6. The method of claim 1, wherein said multiple phases comprise a wetting fluid and a non-wetting fluid.

7. The method of claim 1, wherein said determining a distribution comprises simulating invasion by a non-wetting fluid phase.

8. The method of claim 1, wherein the representation is a graph showing a dependence of a distribution of standard deviation of subvolume porosity on saturation.

9. The method of claim 1, further comprising displaying said representation to a user.

10. The method of claim 1, further comprising comparing said representation for a full pore-matrix model to said representation for a portion of the pore-matrix model to find a multiphase representative elementary volume (REV).

11. A digital rock analysis system that comprises:
a memory having software; and
one or more processors coupled to the memory to execute the software, the software causing the one or more processors to:
derive from a pore-matrix model at least one pore structure parameter;
determine a distribution of multiple phases within pores of the pore matrix model;
based on said distribution, partition the pore-matrix model into multiple phase-matrix models;
derive from each phase-matrix model said at least one pore structure parameter; and
produce a representation of the at least one pore structure parameter's dependence on said distribution.

12. The system of claim 11, wherein the at least one pore structure parameter comprises: a distribution of standard deviation of subvolume porosity and a distribution of standard deviation of subvolume pore surface-to-volume ratio.

13. The system of claim 12, wherein the software further causes the one or more processors to adjust a subvolume length scale until moments of said distributions of standard deviation converge to indicate a multiphase representative elementary volume (REV) size.

14. The system of claim 11, wherein the software further causes the one or more processors to convert one or more images of a sample into said pore-matrix model.

15. The system of claim 14, wherein the software further causes the one or more processors to acquire said one or more images with a scanning microscope.

16. The system of claim 11, wherein said multiple phases comprise a wetting fluid and a non-wetting fluid.

17. The system of claim 11, wherein as part of said determining a distribution the software causes the one or more processors to simulate invasion by a non-wetting fluid phase.

18. The system of claim 11, wherein the representation is a graph showing a dependence of a distribution of standard deviation of subvolume porosity on saturation.

19. The system of claim 11, wherein the software further causes the one or more processors to display said representation to a user.

20. The system of claim 11, wherein the software further causes the one or more processors to compare said representation for a full pore-matrix model to said representation for a portion of the pore-matrix model to find a multiphase representative elementary volume (REV).

* * * * *